(12) United States Patent
Kim et al.

(10) Patent No.: US 8,329,792 B2
(45) Date of Patent: Dec. 11, 2012

(54) PHOSPHONATE BASED COMPOUND AND FLAMEPROOF THERMOPLASTIC RESIN COMPOSITION INCLUDING THE SAME

(75) Inventors: Woo Joong Kim, Uiwang-si (KR); Seung Shik Shin, Uiwang-si (KR); Jin Hwan Choi, Uiwang-si (KR)

(73) Assignee: Cheil Industries Inc., Gumi-si (KR)

( * ) Notice: Subject to any disclaimer, the term of this patent is extended or adjusted under 35 U.S.C. 154(b) by 52 days.

(21) Appl. No.: 12/965,016

(22) Filed: Dec. 10, 2010

(65) Prior Publication Data

US 2011/0160366 A1    Jun. 30, 2011

(30) Foreign Application Priority Data

Dec. 31, 2009    (KR) .................. 10-2009-0135019

(51) Int. Cl.
*C08K 5/00* (2006.01)
*C08K 5/49* (2006.01)

(52) U.S. Cl. ...................................... 524/123; 524/120

(58) Field of Classification Search ............ 524/123
See application file for complete search history.

(56) References Cited

U.S. PATENT DOCUMENTS

2006/0258816 A1    11/2006    Endo

FOREIGN PATENT DOCUMENTS

JP    2002-037973 A    2/2002
WO    2004/087809 A1    10/2004

*Primary Examiner* — Hui Chin
(74) *Attorney, Agent, or Firm* — Summa, Additon & Ashe, P.A.

(57) ABSTRACT

The present invention provides a phosphonate based compound represented by the following Chemical Formula 1 and a flameproof thermoplastic resin composition comprising (A) a thermoplastic resin and (B) a phosphonate based compound represented by the following Chemical Formula 1. The flameproof thermoplastic resin composition can exhibit good flame retardancy and impact strength. Further, the composition does not include a halogenated flame retardant and thus can provide environmental and safety benefits.

[Chemical Formula 1]

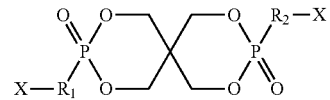

wherein $R_1$ and $R_2$ are each independently $C_1$-$C_4$ alkylene and X is a cyano group.

18 Claims, 1 Drawing Sheet

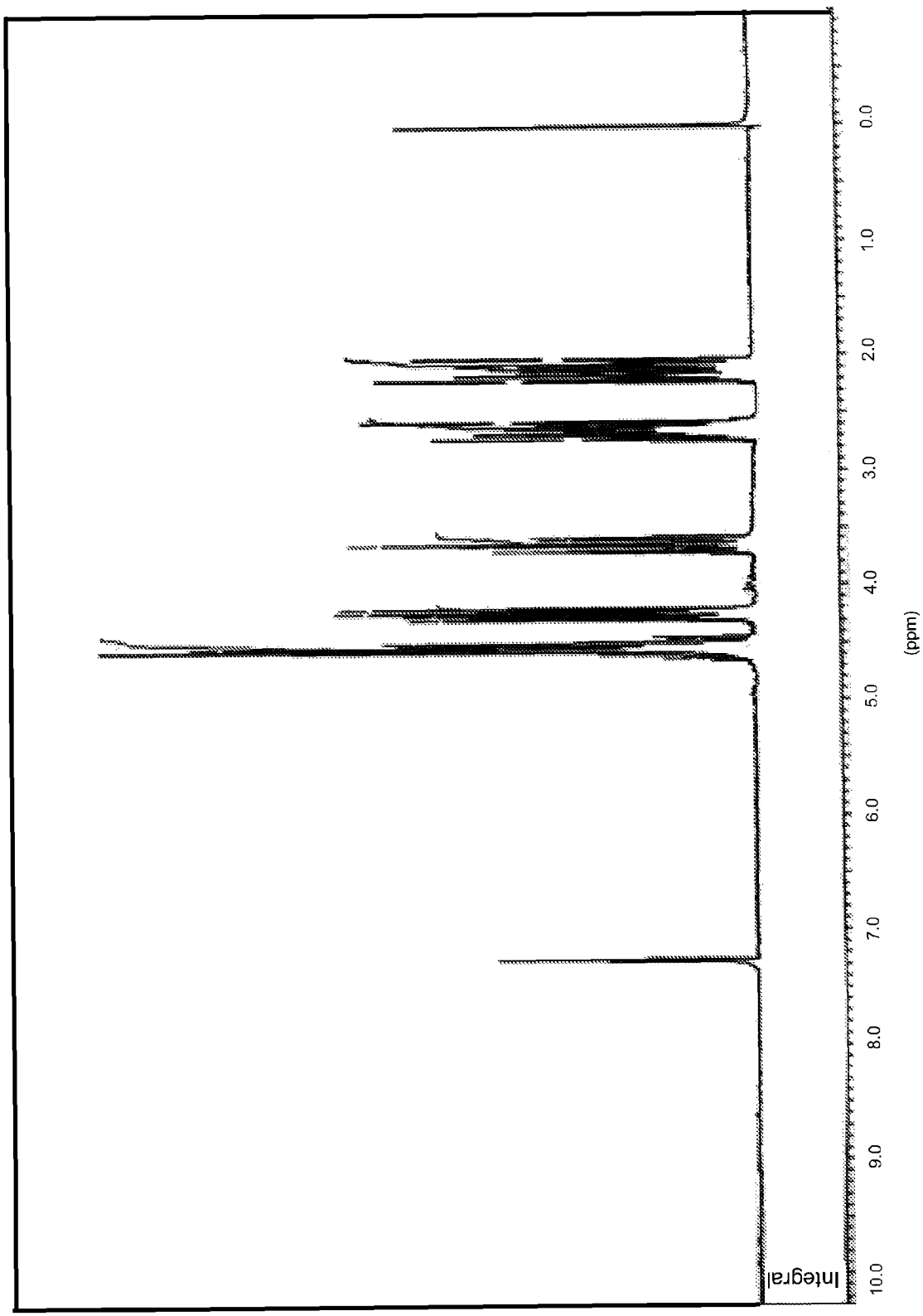

PHOSPHONATE BASED COMPOUND AND FLAMEPROOF THERMOPLASTIC RESIN COMPOSITION INCLUDING THE SAME

CROSS-REFERENCE TO RELATED APPLICATION

This application claims priority from Korea Patent Application No. 2009-0135019, filed on Dec. 31, 2009, in the Korean Intellectual Property Office, the disclosure of which is incorporated herein by reference in its entirety.

FIELD OF THE INVENTION

The present invention relates to a phosphonate based compound and a flameproof thermoplastic resin composition including the same.

BACKGROUND OF THE INVENTION

There has been extensive research directed to the development of flame retardant thermoplastic resin compositions. Conventional methods for imparting flame retardancy to thermoplastic resins include blending the thermoplastic resin composition with a flame retardant agent, such as an antimony-containing, halogen-containing, phosphorus-containing or nitrogen-containing compound.

For example, one conventional technique for imparting flame retardancy to a thermoplastic resin includes adding a halogen-containing flame retardant and an antimony-containing compound to the resin composition. Halogen-containing flame retardants and antimony-containing compounds can impart a desired level of flame retardancy to thermoplastic resin products without significantly degrading the physical properties thereof. However, there is concern regarding the effect of hydrogen halide gases released by halogen-containing compounds during processing on the human body. In this regard, polybromodiphenyl ether, which is widely used as a halogen-containing flame retardant, may produce toxic gases such as dioxin or furan during combustion and thus can be harmful to humans and the environment. Accordingly, there is a need to develop flame retardancy methods that do not employ halogen-containing compounds.

Currently the most common method for imparting flame retardancy without using halogen-containing flame retardants uses a phosphate ester flame retardant. However, the phosphate ester flame retardant has a disadvantage in that it is necessary to add an excessive amount in order to obtain a certain level of flame retardancy.

International Publication No. WO 2004/087809 and Japanese Publication No. 2002-037973 disclose a pentaerythritol alkyl phosphonate compound and an addition type of flameproof resin employing the same. However, these documents do not disclose a method of preparing a phosphoric flameproof compound, which uses a cyanide alkyl phosphonate group derivative with a pentaerythritol compound, and a thermoplastic resin composition including the same.

SUMMARY OF THE INVENTION

The present invention provides a novel phosphonate based compound, which can be added to a resin composition to impart flame retardancy.

The present invention further provides a flameproof thermoplastic resin composition including the novel phosphonate based compound. Because the novel phosphonate based compound of the invention does not include halogen, the present invention can further provide an environmentally friendly flameproof thermoplastic resin. Further, the flameproof thermoplastic resin composition of the invention can exhibit improved flame retardancy as compared to the same composition but with a conventional phosphate ester based flame retardant.

In exemplary embodiments of the present invention, there is provided a phosphonate based compound represented by the following Chemical Formula 1:

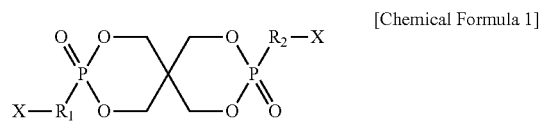

[Chemical Formula 1]

wherein $R_1$ and $R_2$ are each independently $C_1$-$C_4$ alkylene and X is a cyano group.

In exemplary embodiments of the present invention, a flameproof thermoplastic resin composition may include (A) a thermoplastic resin and (B) a phosphonate based compound represented by the above Chemical Formula 1.

In exemplary embodiments of the present invention, (A) the thermoplastic resin can include polystyrene resin (PS), acrylonitrile-butadiene-styrene copolymer resin (ABS), rubber modified polystyrene resin (HIPS), acrylonitrile-styrene-acrylate copolymer resin (ASA), acrylonitrile-styrene copolymer resin (SAN), methyl methacrylate-butadiene-styrene copolymer resin (MBS), acrylonitrile-ethyl acrylate-styrene copolymer resin (AES), polyphenylene ether resin (PPE), polyethylene resin (PE), polypropylene resin (PP), polyethylene terephthalate resin (PET), polybutylene terephthalate resin (PBT), polyvinyl chloride resin (PVC), polymethyl methacrylate resin (PMMA), polyamide resin (PA), and the like, and combinations thereof.

In exemplary embodiments of the present invention, the flameproof thermoplastic resin composition may include (A) about 100 parts by weight of a thermoplastic resin and (B) about 0.5 to about 30 parts by weight of a phosphonate based compound represented by the above Chemical Formula 1.

In exemplary embodiments of the present invention, the flameproof thermoplastic resin composition may further comprise (C) about 1 to about 20 parts by weight of a phosphoric compound.

In exemplary embodiments of the present invention, (C) the phosphoric compound can include (C-1) an aromatic phosphate ester compound or (C-2) an alkyl phosphinic acid metal salt compound, the particle size of which is less than 10 μm.

BRIEF DESCRIPTION OF THE DRAWINGS

FIG. 1 illustrates a $^1$H-NMR analysis result of 2,4,8,10-tetraoxa-3,9-diphosphaspiro[5,5]undecane, 3,9-dicyanoethyl-3,9-dioxide prepared in an exemplary embodiment of the present invention.

DETAILED DESCRIPTION OF THE INVENTION

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

In exemplary embodiments of the present invention, there is provided a phosphonate based compound or a combination of compounds represented by the following Chemical Formula 1:

[Chemical Formula 1]

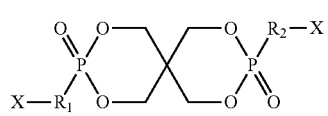

wherein $R_1$ and $R_2$ are each independently $C_1$-$C_4$ alkylene and X is a cyano group.

Examples of the phosphonate based compound represented by the above Chemical Formula 1 may include without limitation 2,4,8,10-tetraoxa-3,9-diphosphaspiro[5,5]undecane, 3,9-dicyanoethyl-3,9-dioxide.

In exemplary embodiments of the present invention, the phosphonate based compound represented by the above Chemical Formula 1 can be prepared by:

reacting a phosphorus trichloride and a pentaerythritol to produce a first reaction intermediate;

reacting the first reaction intermediate with methanol or with NC—R—OH (wherein R is $C_1$-$C_4$ alkylene) to produce a second reaction intermediate and remove hydrochloric acid; and reacting the second reaction intermediate and NC—R—Br (again wherein R is $C_1$-$C_4$ alkylene) to produce a compound of Chemical Formula 1.

The phosphonate based compound represented by the above Chemical Formula 1 can be prepared by the following reaction mechanism. In the following reaction mechanism, R is $C_1$-$C_4$ alkylene.

[Reaction Mechanism]

For example, 2,4,8,10-tetraoxa-3,9-diphosphaspiro[5,5] undecane, 3,9-dicyanoethyl-3,9-dioxide can be prepared by stirring a mixture of a phosphorus trichloride with equivalence ratio of 1 to 3, for example 2, a pentaerythritol with equivalence ratio of 1, and a methanol or a 3-hydroxypropionitrile with equivalence ratio of 2 under nitrogen gas at room temperature to produce a 2,4,8,10-tetraoxa-3,9-diphosphaspiro[5,5]undecane, 3,9-dimethoxy or a 2,4,8,10-tetraoxa-3,9-diphosphaspiro[5,5]undecane, 3,9-dicyanoethoxy, then adding a 3-bromopropionitrile with equivalence ratio of 1 to 3, for example 2 to 2,4,8,10-tetraoxa-3,9-diphosphaspiro[5,5]undecane, 3,9-dimethoxy or 2,4,8,10-tetraoxa-3,9-diphosphaspiro[5,5]undecane, 3,9-dicyanoethoxy, and then stirring a mixture thereof at 100 to 150° C. to produce the 2,4,8,10-tetraoxa-3,9-diphosphaspiro[5,5]undecane, 3,9-dicyanoethyl-3,9-dioxide.

In exemplary embodiments of the present invention, a flameproof thermoplastic resin composition may include (A) a thermoplastic resin and (B) a phosphonate based compound or a combination of compounds represented by the following Chemical Formula 1.

[Chemical Formula 1]

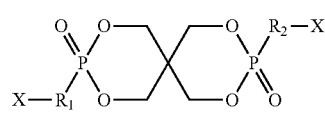

wherein $R_1$ and $R_2$ are each independently $C_1$-$C_4$ alkylene and X is a cyano group.

In exemplary embodiments of the present invention, the flameproof thermoplastic resin composition may include (A) about 100 parts by weight of the thermoplastic resin and (B) about 0.5 to about 30 parts by weight, for example about 5 to about 25 parts by weight, of the phosphonate based compound represented by the above Chemical Formula 1. In some embodiments, the flameproof thermoplastic resin composition may include (B) the phosphonate based compound represented by Chemical Formula 1 in an amount of about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 parts by weight. Further, according to some embodiments of the present invention, the amount of (B) the phosphonate based compound represented by Chemical Formula 1 can be in a range from about any of the foregoing amounts to about any other of the foregoing amounts.

If the phosphonate based compound represented by the above Chemical Formula 1 is employed in an amount of less than about 0.5 parts by weight, the flame retardancy of the

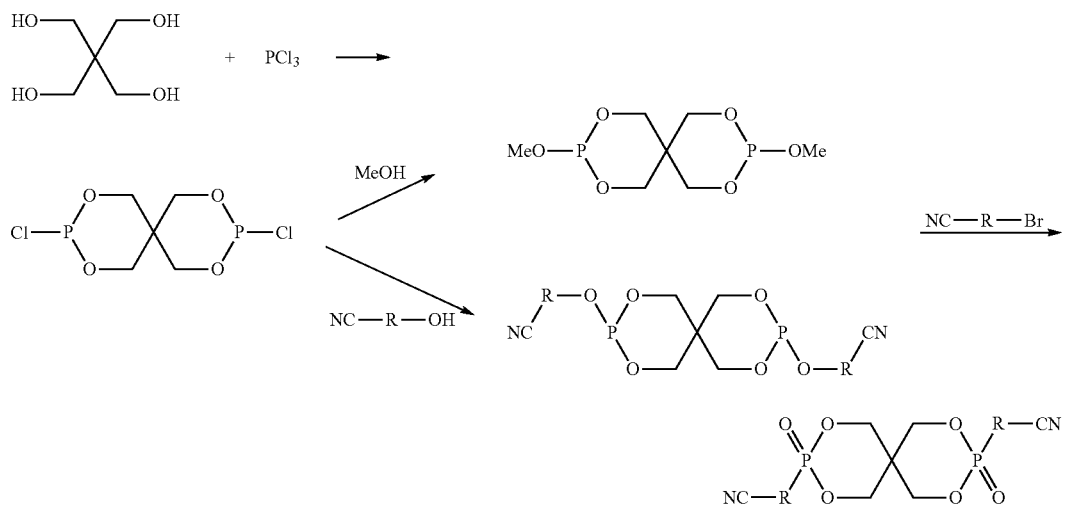

flameproof thermoplastic resin composition may be deteriorated, and if it is employed in an amount of more than about 30 parts by weight, the mechanical properties thereof may be deteriorated.

Examples of the thermoplastic resin can include without limitation polystyrene resin (PS), acrylonitrile-butadiene-styrene copolymer resin (ABS), rubber modified polystyrene resin (HIPS), acrylonitrile-styrene-acrylate copolymer resin (ASA), acrylonitrile-styrene copolymer resin (SAN), methyl methacrylate-butadiene-styrene copolymer resin (MBS), acrylonitrile-ethyl acrylate-styrene copolymer resin (AES), polyphenylene ether resin (PPE), polyolefin resin such as polyethylene resin (PE), polypropylene resin (PP), and the like, polyester resin such as polyethylene terephthalate resin (PET), polybutylene terephthalate resin (PBT), and the like, polyvinyl chloride resin (PVC), polymethyl methacrylate resin (PMMA), polyamide resin (PA), and the like, copolymers thereof, and combinations thereof.

In exemplary embodiments of the present invention, the flameproof thermoplastic resin composition can include (A-1) a styrenic resin, (A-2) a polyphenylene ether resin, and (B) the phosphonate based compound represented by the above Chemical Formula 1. For example, the flameproof thermoplastic resin composition can include about 100 parts by weight of a base resin comprising (A-1) about 70 to about 99% by weight, for example about 70 to about 85% by weight, of the styrenic resin and (A-2) about 1 to about 30% by weight, for example about 15 to about 30% by weight, of the polyphenylene ether resin, and (B) about 0.5 to about 30 parts by weight of the phosphonate based compound represented by the above Chemical Formula 1.

In some embodiments, the base resin can include the styrenic resin (A-1) in an amount of about 70, 71, 72, 73, 74, 75, 76, 77, 78, 79, 80, 81, 82, 83, 84, 85, 86, 87 88, 89, 90, 91, 92, 93, 94, 95, 96, 97, 98, or 99% by weight. Further, according to some embodiments of the present invention, the amount of the styrenic resin (A-1) can be in a range from about any of the foregoing amounts to about any other of the foregoing amounts.

In some embodiments, the base resin can include the polyphenylene ether resin (A-2) in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% by weight. Further, according to some embodiments of the present invention, the amount of the polyphenylene ether resin (A-2) can be in a range from about any of the foregoing amounts to about any other of the foregoing amounts.

If (A-2) the polyphenylene ether resin is employed in an amount of less than about 1% by weight, the flame retardancy of the flameproof thermoplastic resin composition may be deteriorated, and if it is employed in an amount of more than about 30% by weight, the moldability may be deteriorated.

In exemplary embodiments of the present invention, the flameproof thermoplastic resin composition may further comprise (C) a phosphoric compound.

In exemplary embodiments of the present invention, (C) the phosphoric compound can include (C-1) an aromatic phosphate ester compound and/or (C-2) an alkyl phosphinic acid metal salt compound, the particle size of which is less than 10

In exemplary embodiments of the present invention, (C) the phosphoric compound may be employed in an amount of about 1 to about 20 parts by weight, for example about 1 to about 10 parts by weight, based on about 100 parts by weight of (A) the thermoplastic resin. In some embodiments, the thermoplastic resin (A) can include the phosphoric compound (C) in an amount of about 1, 2, 3, 4, 5, 6, 7, 8, 9, 10, 11, 12, 13, 14, 15, 16, 17, 18, 19, or 20 parts by weight. Further, according to some embodiments of the present invention, the amount of the phosphoric compound (C) can be in a range from about any of the foregoing amounts to about any other of the foregoing amounts.

In exemplary embodiments of the present invention, (C-1) the aromatic phosphate ester compound may include a compound or a combination of compounds represented by the following Chemical Formula 2.

[Chemical Formula 2]

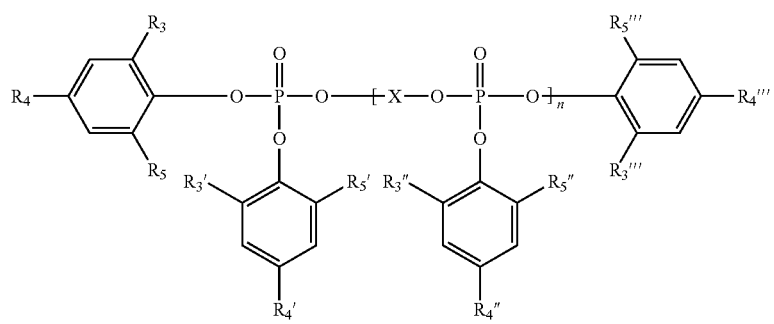

wherein $R_3$, $R_4$, $R_5$, $R_3'$, $R_4'$, $R_5'$, $R_3''$, $R_4''$, $R_5''$, $R_3'''$, $R_4'''$ and $R_5'''$ are each independently hydrogen or $C_1$-$C_4$ alkyl, X is $C_6$-$C_{20}$ aryl or $C_1$-$C_4$ alkyl-substituted $C_6$-$C_{20}$ aryl, and n is an integer from 0 to 4.

In exemplary embodiments of the present invention, X is derived from a dialcohol such as resorcinol, hydroquinol, or bisphenol-A.

When n is 0, examples of the aromatic phosphate ester compound represented by the above Chemical Formula 2 can include without limitation triphenyl phosphate, tri(2,6-dimethyl) phosphate, and the like. When n is 1, examples of the aromatic phosphate ester compound represented by the above Chemical Formula 2 can include without limitation resorcinol bis(diphenyl) phosphate, resorcinol bis(2,6-dimethyl phenyl) phosphate, resorcinol bis(2,4-ditertiary butyl phenyl) phosphate, hydroquinol bis(2,6-dimethyl phenyl) phosphate, hydroquinol bis(2,4-ditertiary butyl phenyl) phosphate, and the like. The aromatic phosphate ester compounds can be used alone or in combination thereof.

In exemplary embodiments of the present invention, (C-2) the alkyl phosphinic acid metal salt compound may include a compound or a combination of compounds represented by the following Chemical Formula 3, and can have an average particle size of less than about 10 μm, for example about 1 to about 10 μM.

[Chemical Formula 3]

$$\left[ \begin{array}{c} O \\ \parallel \\ R-P-R \\ | \\ O \end{array} \right]_n^- M^{n+}$$

wherein each R is independently $C_1$-$C_6$ alkyl, $C_1$-$C_6$ cycloalkyl or $C_6$-$C_{10}$ aryl, M is a metal, such as Al, Zn, Ca, and the like, and n is an integer of 2 or 3.

In exemplary embodiments of the present invention, R is methyl, ethyl, propyl, butyl or phenyl, and M is Al or Zn.

In some embodiments, the alkyl phosphinic acid metal salt compound (C-2) can have an average particle size of about 1, 2, 3, 4, 5, 6, 7, 8, 9, or 10 μm. Further, according to some embodiments of the present invention, the average particle, size of the alkyl phosphinic acid metal salt compound (C-2) can be in a range from about any of the foregoing sizes to about any other of the foregoing sizes.

The flameproof thermoplastic resin composition according to the present invention may further include one or more other additives depending on its use. Examples of such additives may include without limitation plasticizers, heat stabilizers, antioxidants, anti-dripping agents, compatibilizers, light-stabilizers, pigments, dyes, and/or inorganic fillers and the like. The additives can be used alone or in combination with one another. Examples of the inorganic fillers include asbestos, glass fibers, talc, ceramic, sulfates, and the like, and combinations thereof. The additives can be added in an amount of about 30 parts by weight or less, for example about 0.001 to about 30 parts by weight, based on about 100 parts by weight of the resin composition including (A) and (B).

The flameproof thermoplastic resin composition of the present invention can be prepared by conventional methods. For example, all the components and optional additives can be mixed together and extruded through an extruder and can be prepared in the form of pellets.

In exemplary embodiments of the present invention, the flameproof thermoplastic resin composition can be molded by conventional methods to provide a molded article. The molded article prepared from the flameproof thermoplastic resin composition according the present invention can exhibit good impact strength and flame retardancy, and can be an environmentally friendly molded article.

Exemplary methods of preparing a molded article from the flameproof thermoplastic resin composition of the present invention may include without limitation extrusion molding, injection molding, vacuum molding, casting molding and the like, and which can be easily carried out by a person with ordinary skill in the art.

The invention may be better understood by reference to the following examples, and which are intended for the purpose of illustration and are not to be construed as in any way limiting the scope of the present invention, which is defined in the claims appended hereto.

EXAMPLES

The component specifications of the flameproof thermoplastic resin compositions used in the Examples and Comparative Examples are as follows:

(A-1) Styrenic Resin

A rubber modified polystyrene resin (HIPS) made by Cheil Industries Inc. of Korea (product name: HG-1760S) is used.

(A-2) Polyphenylene Ether Resin

A poly(2,6-dimethyl-phenylether) with an average particle size of ten μm in the form of powder made by Mitsubishi Engineering Plastics Corp. of Japan (product name: PX-100F) is used.

(A-3) PET Resin

A polyethylene terephthalate resin with an intrinsic viscosity of 0.8 and a melting point of 254° C. made by SK Chemicals of Korea (product name: BB-8055) is used.

(A-4) ABS Resin

An acrylonitrile-butadiene-styrene copolymer resin made by Cheil Industries Inc. of Korea (product name: SD-0150) is used.

(B) Phosphonate Based Compound

A mixture of 274.6 g (2 mol) of a phosphorus trichloride, 136.1 g (1 mol) of a pentaerythritol and 64.08 g (2 mol) of a methanol or 142.06 g (2 mol) of a 3-hydroxypropionitrile is stirred in a nitrogen gas at room temperature for 3 hours. Then 265.9 g (2 mol) of a 3-bromopropionitrile is added into the mixture, and then the mixture thereof is stirred in a nitrogen gas at 150° C. for 12 hours. After the completion of the reaction, the temperature of the product is reduced to room temperature, and the product is washed with dimethyl ether to obtain a 2,4,8,10-tetraoxa-3,9-diphosphaspiro[5,5]undecane, 3,9-dicyanoethyl-3,9-dioxide with a purity of more than about 98% and a yield of about 94%.

(C-1) Aromatic Phosphate Ester Compound

A bis(dimethyl phenyl)phosphate bisphenol-A made by DAIHACHI Chemical Industry Co., Ltd. of Japan (product name: CR741S) is used.

(C-2) Alkyl Phosphinic Acid Metal Salt Compound

An aluminum diethyl phosphinate made by Clariant Corp. (product name: Exolit OP930) is used.

Examples 1-13 and Comparative Examples 1-8

The above-mentioned components are added in the amounts set forth in the following Table 1 and Table 2 to a conventional mixer and the mixture is extruded through a conventional twin screw extruder at a temperature of about 240° C. to prepare pellets. The prepared pellets are dried at 80° C. for 2 hours and molded into test specimens for flame retardancy in an injection molding machine at about 230° C. with a mold temperature of about 50° C. The flame retardancy of the prepared test specimens is measured in accordance with UL 94 VB under a thickness of ⅛", and the impact strength thereof is measured in accordance with ASTM D256. The results are shown in Table 1 and Table 2.

TABLE 1

|  | Examples | | | | | | | | | | | | |
| --- | --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 | 13 |
| (A-1) HIPS | 100 | 100 | 100 | 90 | 90 | 90 | 80 | 80 | 80 |  |  |  |  |
| (A-2) PPE | 0 | 0 | 10 | 10 | 10 | 10 | 20 | 20 | 20 |  |  |  |  |
| (A-3) PET |  |  |  |  |  |  |  |  |  | 100 | 100 |  |  |
| (A-4) ABS |  |  |  |  |  |  |  |  |  |  |  | 100 | 100 |

TABLE 1-continued

| | Examples | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| (B) Phosphonate based compound | 20 | 15 | 15 | 20 | 15 | 15 | 20 | 15 | 15 | 20 | 10 | 20 | 10 |
| (C-1) Aromatic phosphate ester compound | | 5 | | | 5 | | | 5 | | | | | |
| (C-2) Alkyl phosphinic acid metal salt compound | | | 5 | | | 5 | | | 5 | | | | |
| UL94 flame retardancy (⅛") | V-1 | V-1 | V-1 | V-0 | V-0 | V-0 | V-0 | V-0 | V-0 | V-0 | V-0 | V-1 | V-1 |
| Total burn time | 64 | 80 | 82 | 35 | 42 | 48 | 29 | 31 | 38 | 28 | 62 | 61 | 79 |
| Impact strength | 5.2 | 5.6 | 5.8 | 5.8 | 6.3 | 6.5 | 5.9 | 6.4 | 6.7 | 5.9 | 6.2 | 6.1 | 6.8 |

TABLE 2

| | Comparative Examples | | | | | | | |
|---|---|---|---|---|---|---|---|---|
| | 1 | 2 | 3 | 4 | 5 | 6 | 7 | 8 |
| (A-1) HIPS | 100 | 100 | 90 | 90 | 80 | 80 | | |
| (A-2) PPE | | | 10 | 10 | 20 | 20 | | |
| (A-3) PET | | | | | | | 100 | |
| (A-4) ABS | | | | | | | | 100 |
| (B) Phosphonate based compound | | | | | | | | |
| (C-1) Aromatic phosphate ester compound | 15 | 5 | 15 | 5 | 15 | 5 | 20 | 20 |
| (C-2) Alkyl phosphinic acid metal salt compound | 5 | 15 | 5 | 15 | 5 | 15 | | |
| UL94 flame retardancy (⅛") | Fail | Fail | Fail | Fail | Fail | Fail | V-1 | Fail |
| Total burn time | — | — | — | — | — | — | 62 | — |
| Impact strength | 2.6 | 3.4 | 2.8 | 3.5 | 3.4 | 3.7 | 5.6 | 6.8 |

As shown above Table 1 and Table 2, Examples 1 to 13 prepared by employing the 2,4,8,10-tetraoxa-3,9-diphosphaspiro[5,5]undecane, 3,9-dicyanoethyl-3,9-dioxide exhibit good flame retardancy and impact strength, compared to Comparative Examples 1 to 8 which do not include 2,4,8,10-tetraoxa-3,9-diphosphaspiro[5,5]undecane, 3,9-dicyanoethyl-3,9-dioxide.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

What is claimed is:

1. A phosphonate based compound or a combination of compounds represented by the following Chemical Formula 1:

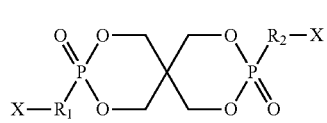

[Chemical Formula 1]

wherein $R_1$ and $R_2$ are each independently $C_1$-$C_4$ alkylene and X is a cyano group.

2. The phosphonate based compound of claim 1, wherein said phosphonate based compound is 2,4,8,10-tetraoxa-3,9-diphosphaspiro[5,5]undecane, 3,9-dicyanoethyl-3,9-dioxide.

3. A flameproof thermoplastic resin composition comprising (A) a thermoplastic resin and (B) a phosphonate based compound or a combination of compounds represented by the following Chemical Formula 1:

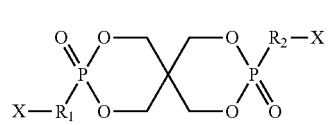

[Chemical Formula 1]

wherein $R_1$ and $R_2$ are each independently $C_1$-$C_4$ alkylene and X is a cyano group.

4. The flameproof thermoplastic resin composition of claim 3, wherein (B) the phosphonate based compound is 2,4,8,10-tetraoxa-3,9-diphosphaspiro[5,5]undecane, 3,9-dicyanoethyl-3,9-dioxide.

5. The flameproof thermoplastic resin composition of claim 3, wherein the thermoplastic resin comprises a polystyrene resin (PS), acrylonitrile-butadiene-styrene copolymer resin (ABS), rubber modified polystyrene resin (HIPS), acrylonitrile-styrene-acrylate copolymer resin (ASA), acrylonitrile-styrene copolymer resin (SAN), methyl methacrylate-butadiene-styrene copolymer resin (MBS), acrylonitrile-ethyl acrylate-styrene copolymer resin (AES), polyphenylene ether resin (PPE), polyethylene resin (PE), polypropylene resin (PP), polyethylene terephthalate resin (PET), polybutylene terephthalate resin (PBT), polyvinyl chloride resin (PVC), polymethyl methacrylate resin (PMMA), polyamide resin (PA), or a combination thereof.

6. The flameproof thermoplastic resin composition of claim 5, comprising (A) about 100 parts by weight of the thermoplastic resin and (B) about 0.5 to about 30 parts by weight of the phosphonate based compound represented by the above Chemical Formula 1.

7. The flameproof thermoplastic resin composition of claim 6, comprising (B) about 5 to about 25 parts by weight of the phosphonate based compound represented by the above Chemical Formula 1.

8. The flameproof thermoplastic resin composition of claim 6, wherein said thermoplastic resin (A) comprises a base resin comprising (A-1) a styrenic resin and (A-2) a polyphenylene ether resin.

9. The flameproof thermoplastic resin composition of claim 8, wherein the base resin comprises (A-1) about 70 to about 99% by weight of said styrenic resin and (A-2) about 1 to about 30% by weight of said polyphenylene ether resin.

10. The flameproof thermoplastic resin composition of claim 9, wherein the base resin comprises (A-1) about 70 to about 85% by weight of said styrenic resin and (A-2) about 15 to about 30% by weight of said polyphenylene ether resin.

11. The flameproof thermoplastic resin composition of claim 10, wherein (B) the phosphonate based compound is 2,4,8,10-tetraoxa-3,9-diphosphaspiro[5,5]undecane, 3,9-dicyanoethyl-3,9-dioxide.

12. The flameproof thermoplastic resin composition of claim 3, further comprising (C) about 1 to about 20 parts by weight of a phosphoric compound.

13. The flameproof thermoplastic resin composition of claim 12, comprising (C) about 1 to about 10 parts by weight of a phosphoric compound.

14. The flameproof thermoplastic resin composition of claim 12, wherein (C) the phosphoric compound comprises (C-1) an aromatic phosphate ester compound, (C-2) an alkyl phosphinic acid metal salt compound with a particle size of less than 10 μm, or a combination thereof.

15. The flameproof thermoplastic resin composition of claim 14, wherein (C-1) the aromatic phosphate ester compound comprises a compound or a combination of compounds represented by the following Chemical Formula 2:

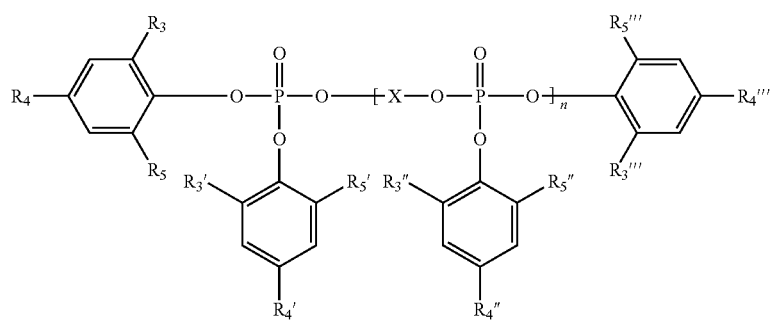

[Chemical Formula 2]

wherein $R_3$, $R_4$, $R_5$, $R_3'$, $R_4'$, $R_5'$, $R_3''$, $R_4''$, $R_5''$, $R_3'''$, $R_4'''$ and $R_5'''$ are each independently hydrogen or $C_1$-$C_4$ alkyl, X is $C_6$-$C_{20}$ aryl or $C_1$-$C_4$ alkyl-substituted $C_6$-$C_{20}$ aryl, and n is an integer from 0 to 4.

16. The flameproof thermoplastic resin composition of claim 14, wherein (C-2) the alkyl phosphinic acid metal salt compound comprises a compound or a combination of compounds represented by the following Chemical Formula 3:

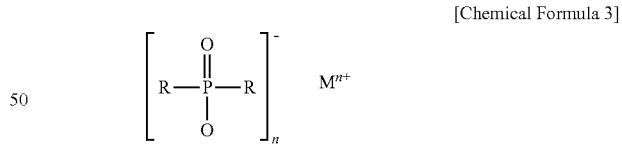

[Chemical Formula 3]

wherein each R is independently $C_1$-$C_6$ alkyl, $C_2$-$C_6$ cycloalkyl or $C_6$-$C_{10}$ aryl, M is a metal comprising Al, Zn or Ca, and n is an integer of 2 or 3.

17. The flameproof thermoplastic resin composition of claim 3, further comprising less than about 30 parts by weight of one or more additives selected from the group consisting of heat stabilizers, antioxidants, anti-dripping agents, compatibilizers, light-stabilizers, pigments, dyes, inorganic fillers, and combinations thereof.

18. A molded article prepared from the flameproof thermoplastic resin composition according to claim 3.

* * * * *